United States Patent
Barth et al.

(10) Patent No.: US 7,087,649 B2
(45) Date of Patent: Aug. 8, 2006

(54) METHODS FOR PREVENTING AND TREATING DISEASES AND CONDITIONS ASSOCIATED WITH CELLULAR STRESS

(75) Inventors: Jay Barth, Teaneck, NJ (US); Yoshiaki Goto, Ibaragi (JP)

(73) Assignee: Eisai Co., Ltd., Tokyo (JP)

( * ) Notice: Subject to any disclaimer, the term of this patent is extended or adjusted under 35 U.S.C. 154(b) by 0 days.

(21) Appl. No.: 10/479,774

(22) PCT Filed: Jun. 7, 2002

(86) PCT No.: PCT/US02/18201

§ 371 (c)(1),
(2), (4) Date: Sep. 24, 2004

(87) PCT Pub. No.: WO02/098398

PCT Pub. Date: Dec. 12, 2002

(65) Prior Publication Data

US 2005/0032911 A1   Feb. 10, 2005

Related U.S. Application Data

(60) Provisional application No. 60/296,604, filed on Jun. 7, 2001.

(51) Int. Cl.
*A61K 31/12* (2006.01)
(52) U.S. Cl. .................................................... 514/675
(58) Field of Classification Search ................ 514/675
See application file for complete search history.

(56) References Cited

U.S. PATENT DOCUMENTS

| | | | |
|---|---|---|---|
| 4,169,157 A | | 9/1979 | Kijima et al. |
| 4,814,353 A | | 3/1989 | Itor et al. |
| 5,190,961 A | * | 3/1993 | Hasegawa et al. ........... 514/331 |
| 2003/0069279 A1 | * | 4/2003 | Sato et al. ................... 514/338 |

OTHER PUBLICATIONS

Cecil Textbook of Medicine, 21st Edition, vol. 1, published 2000 by W.B. Saunders Company (PA), pp. 50, 51, 658-663 and 66 679.*

The Merck Manual of Diagnosis and Therapy, 14th Edition, published 1982 by Merck, Sharp & Dohme Research Laboratories, pp. 720, 721, 724-731.*

Kondo, "An Experimental and Clinical Study of Gastric Mucosal Damage Induced by Alcohol", Tokyo Jikeikai Medical Journal, (1991), vol. 106, No. 1, pp. 163-180 (BIOSIS Abstract only, AN:1991:279055).*

Terano et al., "Tetraprenylacetone Promotes Healing Process of Ethanol-Induced Gastric damage in the Rat", Japanese Journ of Pharmacology, (Jan. 1991), 55(1), 115-20 (MEDLINE Abstract only, AN: 91251405).*

* cited by examiner

Primary Examiner—Raymond J. Henley, III
(74) Attorney, Agent, or Firm—Clark & Elbing LLP

(57) ABSTRACT

This invention relates to methods of preventing and treating diseases and conditions associated with cellular stress. The methods involve administration of an effective amount of a compound of the formula:

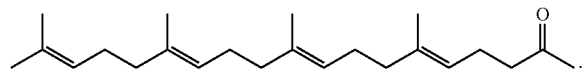

8 Claims, No Drawings

METHODS FOR PREVENTING AND TREATING DISEASES AND CONDITIONS ASSOCIATED WITH CELLULAR STRESS

CROSS-REFERENCE TO RELATED APPLICATIONS

This application claims priority under 35 U.S.C. § 371 from PCT/US02/18201, filed Jun. 7, 2002, which claims priority under 35 U.S.C. § 119 from application U.S. Ser. No. 60/296,604, filed Jun. 7, 2001 (now abandoned).

FIELD OF THE INVENTION

This invention relates to methods of preventing and treating diseases and conditions associated with cellular stress.

BACKGROUND OF THE INVENTION

The body responds to cellular stress by a highly conserved response that includes the induction of a family of proteins known as stress proteins, which are also referred to as heat shock proteins and chaperones. These proteins play essential roles in the normal functioning of cells, and also have been implicated in several diseases and conditions, including heart disease, diabetes, autoimmune disease, cancer, and cellular stress caused by, for example, exposure to high temperatures, low oxygen levels (i.e., ischemia), inflammation, infection, heavy metal exposure, and alcohol.

Consumption of ethanol-containing drinks, such as beer, wine, and liquor, can cause cellular stress in, and thereby induce or exacerbate a number of conditions of, the gastrointestinal tract including, for example, gastritis, abdominal pain, gastrointestinal distress, dyspepsia, and ulcers. In addition, excessive alcohol consumption can cause the physical discomforts often felt by persons the morning after such consumption, which are collectively known as hangover. The severity of a hangover depends on several factors, including the ability of the person to process alcohol, the non-alcoholic components of the drinks (called congeners), the amount of alcohol consumed over a particular time period, and the severity of the dehydration caused by the excessive alcohol consumption. There are many supposed treatments for hangover, including black coffee and further consumption in the morning of small amounts of alcohol. None of these measures adequately treats the symptoms of hangover, which can include abdominal discomfort, nausea, fatigue, and headache.

SUMMARY OF THE INVENTION

This invention provides methods of ameliorating one or more symptoms of a disease or condition associated with cellular stress. For example, the methods of the invention can be used in the prevention or treatment of an alcohol-induced or alcohol-exacerbated injury to, or condition of, the gastrointestinal tract. As a specific example, the methods of the invention can be used in the prevention and treatment of hangover. Additional examples of diseases and conditions that can be prevented or treated using the methods of the invention are provided below.

The methods of the invention involve use of a drug known as SELBEX® (geranylgeranylacetone), which has the formula:

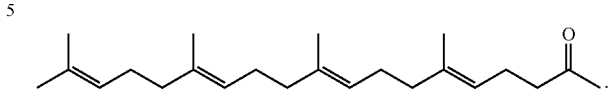

SELBEX® (geranylgeranylacetone) is a drug that was first marketed by Eisai Co., Ltd. in Japan in 1994 for the treatment of peptic ulcers. SELBEX® (geranylgeranylacetone), its synthesis, and its formulations are described in U.S. Pat. No. 4,169,157, which is incorporated herein by reference.

According to the invention, administration of SELBEX® (geranylgeranylacetone) is carried out to ameliorate one or more symptoms of gastrointestinal injuries or conditions such as, for example, hangover, non-steroidal anti-inflammatory drug (NSAID)-induced gastroduodenal injury (caused by, e.g., aspirin, acetaminophen, or ibuprophen), gastritis, dyspepsia, nausea, gastrointestinal distress, abdominal pain, esophagitis, gastroesophageal reflux disease (GERD), colitis, irritable bowel syndrome, inflammatory bowel disease (including Crohn's disease and ulcerative colitis), diverticulosis, diverticulitis, celiac disease, Zollinger-Ellison disease, *Helicobacter pylori* infection, heartburn, hiatal hernia, and Barrett's esophagus. Additional examples of diseases and conditions that can be prevented or treated using the methods of the invention are provided below.

When used to prevent or to treat hangover, the administration can take place, for example, either: (i) within two hours prior to drinking an alcoholic beverage; (ii) during the drinking of alcoholic beverages; (iii) within one hour after drinking the last in a series of alcoholic beverages; (iv) within fourteen hours after drinking the last in a series of alcoholic beverages; or (v) at two or more of the time points specified in (i)–(iv).

The total amount of SELBEX® (geranylgeranylacetone) administered over a fourteen hour period can be, for example, 10–1,000 mg, e.g., 50–500 mg, e.g., 100–300 mg, as determined to be appropriate by those of skill in this art. The amount of SELBEX® (geranylgeranylacetone) administered can vary, depending on the body weight of the patient, the alcohol tolerance of the patient, and the amount of alcohol consumed. The invention also includes the use of SELBEX® (geranylgeranylacetone) in the preparation of medicaments for preventing and treating the diseases and conditions described herein.

The methods of the invention are effective and produce little in the way of side effects. Other features and advantages of the invention will be apparent from the following detailed description and from the claims.

DETAILED DESCRIPTION

The invention provides methods of ameliorating one or more symptoms of diseases or conditions associated with the induction of cellular stress. As a specific example, the methods of the invention can be used to prevent or to treat alcohol-induced or alcohol-exacerbated injury to, or discomfort in, the gastrointestinal tract. For example, the methods of the invention can be used to prevent or to treat the symptoms of hangover. The methods of the invention can also be used to prevent or to treat alcohol-induced or alcohol-exacerbated NSAID-induced gastroduodenal injury, gastritis, dyspepsia, nausea, gastrointestinal distress, abdominal pain, esophagitis, gastroesophageal reflux disease (GERD), colitis, irritable bowel syndrome, inflammatory bowel disease (including Crohn's disease and ulcerative colitis), diverticulosis, diverticulitis, celiac disease, Zollinger-Ellison disease, *Helicobacter pylori* infection, heartburn, hiatal hernia, Barrett's esophagus, and other gastrointestinal diseases and conditions. In addition, the methods of the invention can be used in the prevention and treatment of these diseases and conditions of the gastrointestinal tract (except, of course, hangover) when alcohol consumption is not involved.

Other diseases and conditions associated with cellular stress can also be prevented or treated using the methods of the present invention. Examples of such diseases and conditions include cardiovascular disease (e.g., heart attack, stroke, atherosclerosis, hypertension, congestive heart failure, and angioplastic restenosis), ischemia reperfusion injury, transient ischemic attack, chronic and acute mesenteric ischemia, critical limb ischemia, alcoholic liver disease, arthritis (e.g., rheumatoid arthritis), neurodegenerative diseases (e.g., Alzheimer's disease and Parkinson's disease), mercury poisoning, prion disease (e.g., Creutzfeld-Jacob disease, bovine spongiform encephalopathy, and scrapie), systemic lupus erythematosus, bacterial and viral infection, septic shock, grain dust fever, mucositis, gingivitis, insulin-dependent diabetes (IDD), neuropathy (e.g., diabetic neuropathy), nephropathy, myopathy, graft versus host disease, prevention of failure or rejection of a transplanted tissue or organ (e.g., liver, kidney, lung, and heart), spinal cord injury, trauma, wound healing, and pulmonary inflammation. As is known in the art, several of these diseases and conditions may be characterized by heat shock protein and/or inflammatory cytokine (e.g., tumor necrosis factor-$\alpha$) induction. Prevention and treatment of other diseases and conditions associated with such induction is also included in the invention.

The invention is based, in part, on a clinical experiment that an inventor of the invention described herein conducted on himself using SELBEX® (geranylgeranylacetone). On one occasion in the evening, he consumed an excessive amount of alcoholic beverages and awoke the following morning experiencing abdominal discomfort, nausea, fatigue, and headache. The normal measures that he had taken in the past to ameliorate hangover provided little relief. He decided that on the next occasion on which he would be drinking alcoholic beverages, he would ingest SELBEX® (geranylgeranylacetone) to determine whether it provided relief. Thus, on a subsequent evening, just prior to the drinking of alcoholic beverages, he ingested 50 mg of SELBEX® (geranylgeranylacetone) orally, in the form of a capsule marketed commercially by Eisai Co., Ltd. During the course of the evening, as he continued drinking alcoholic beverages, he ingested an additional 50 mg of SELBEX® (geranylgeranylacetone) orally. The next morning when he awoke, he ingested an additional 50 mg of SELBEX® (geranylgeranylacetone), bringing the total ingested during a fourteen hour period to 150 mg. Although he had consumed as much alcohol as on the previous occasion, the above-described symptoms were either abolished or markedly alleviated by SELBEX® (geranylgeranylacetone).

Synthesis

SELBEX® (geranylgeranylacetone) can be synthesized according to the method described in U.S. Pat. No. 4,169, 157, which, as is noted above, is incorporated herein by reference. Nonproprietary names of SELBEX® (geranylgeranylacetone) are teprenone and geranylgeranylacetone, and its chemical name is 3:2 (5E:5Z) geometrical mixture of (9E,13E)-6,10,14,18-tetramethyl-5,9,13,17-nonadecatetraen-2-one. The molecular formula of SELBEX® (geranylgeranylacetone) is $C_{23}H_{38}O$, giving it a molecular weight of 330.55. Teprenone occurs as colorless to pale yellow, oily liquid. It has a faint characteristic odor and is tasteless. It is miscible with methanol, ethanol, acetone, chloroform, and hexane; is practically insoluble in water; and is affected by air.

Formulation

SELBEX® (geranylgeranylacetone) can be administered according to the methods of the invention in any form suitable for oral administration, including capsule, powder, tablet, granule, pill, or liquid forms. In addition, SELBEX® (geranylgeranylacetone) can be administered parenterally by injection or it can be administered as a suppository. Many suitable formulations are described in U.S. Pat. No. 4,169, 157. A preferred formulation is a capsule that includes 50 mg SELBEX® (geranylgeranylacetone) and, as inactive ingredients, tocopherol, sodium lauryl sulfate, and, if desired, pharmaceutically acceptable agents to provide color (e.g., FD&C Blue No. 1 and FD&C Yellow No. 6). Another preferred formulation consists of fine granules, in which each gram of white to yellowish granules contains 100 mg of SELBEX® (geranylgeranylacetone). Tocopherol can also be included in this formulation as an inactive ingredient. Other pharmaceutically acceptable formulations can be prepared, as can be determined by those of skill in this art. (See, e.g., *Remington's Pharmaceutical Sciences* ($18^{th}$ edition), ed. A. Gennaro, 1990, Mack Publishing Company, Easton, Pa., for additional examples of formulations that can be used.)

Dosage and Timing of Administration

SELBEX® (geranylgeranylacetone) can be administered at any time before or during the occurrence of alcohol-induced (or exacerbated) injury or discomfort in the gastrointestinal tract, such as the symptoms or hangover or other diseases and conditions, such as those listed herein. Examples of SELBEX® (geranylgeranylacetone) administration regimens are as follows.

SELBEX® (geranylgeranylacetone) can be used according to the methods of the invention in a purely prophylactic mode, in which a person self-administers, for example, 20–100 mg of SELBEX® (geranylgeranylacetone) orally, for example, just prior to the beginning of a period of alcohol consumption.

Alternatively, SELBEX® (geranylgeranylacetone) can be administered after alcohol consumption has begun, for example, dosages of 10–30 mg can be self-administered every 1–3 hours, for a total of 50–100 mg as 2–5 separate administrations.

SELBEX® (geranylgeranylacetone) can be used according to the invention, alternatively, purely in a treatment mode, i.e., to alleviate the symptoms of hangover in the morning following a period of excessive drinking. In this case, SELBEX® (geranylgeranylacetone) can be administered, for example, 1–4 times orally, for a total dosage of 20–200 mg.

SELBEX® (geranylgeranylacetone) can also be administered prior to, during, and/or after alcohol consumption, in any appropriate combination. For example, it can be administered prior to consumption of alcoholic beverages, at some point during consumption, and after consumption, on the same day and/or on the next day. Preferably, when two or three administration modes are used, the total amount of SELBEX® (geranylgeranylacetone) administered is at least 50 mg over a fourteen hour period, and does not exceed 500–1,000 mg in that period.

Similar regimens and dosages of SELBEX® (geranylgeranylacetone) can be used to prevent or treat conditions such as NSAID-induced gastroduodenal injury, gastritis, dyspepsia, nausea, gastrointestinal distress, abdominal pain, colitis, irritable bowel syndrome, inflammatory bowel disease, diverticulosis, diverticulitis, celiac disease, whether or not induced or exacerbated by alcohol consumption, and other diseases or conditions mentioned herein. In cases in which alcohol consumption is not involved, treatment can be carried out for two or more days, e.g., for 1 week to 10 days, as needed to alleviate symptoms. Treatment may be required for relatively short periods of time (e.g., days, weeks, or months) or, alternatively, may be required continuously over many years.

When used to prevent or to treat diseases and conditions of the gastrointestinal tract, SELBEX® (geranylgeranylacetone) can be administered alone or, alternatively, in combination with one or more proton pump inhibitors. Examples of proton pump inhibitors that can be used in the invention include, rabeprazole (AcipHex), omeprazole (Prilosec), lansoprazole (Prevacid), esomeprazole (Nexium), or pantoprazole (Protonix). Appropriate amounts of these agents to be used in the invention can readily be determined by those of skill in this art and can range, for example, from 1–100 mg/day, e.g., 10–60 or 20–40 mg/day.

Other embodiments are within the following claims.

The invention claimed is:

1. A method of ameliorating one or more symptoms of an alcohol-induced or alcohol-exacerbated injury to, or condition of, the gastrointestinal tract in a person, said method comprising administering to said person an effective amount of a compound of the formula:

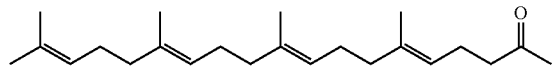

wherein the injury or condition is selected from the group consisting of hangover, Crohn's disease, and ulcerative colitis.

2. The method of claim 1, wherein said injury or condition is hangover.

3. The method of claim 1, wherein administration is carried out either: (i) within two hours prior to drinking an alcoholic beverage; (ii) during the period of drinking alcoholic beverages; (iii) within one hour after drinking the last in a series of alcoholic beverages; (iv) within fourteen hours after drinking the last in a series of alcoholic beverages; or (v) two or more of (i)–(iv).

4. The method of claim 1, wherein the total amount of said compound administered over a fourteen-hour period is 10–1,000 mg.

5. The method of claim 4, wherein the total amount of said compound administered in said period is 50–500 mg.

6. The method of claim 5, wherein the total amount of said compound administered is 100–300 mg.

7. The method of claim 1, wherein the injury or condition is Crohn's disease.

8. The method of claim 1, wherein the injury or condition is ulcerative colitis.

* * * * *